(12) United States Patent
Krause et al.

(10) Patent No.: US 9,492,893 B2
(45) Date of Patent: Nov. 15, 2016

(54) METHOD AND ARRANGEMENT FOR MANUFACTURING A SAMPLE FOR MICROSTRUCTURAL MATERIALS DIAGNOSTICS AND CORRESPONDING SAMPLE

(71) Applicant: Fraunhofer-Gesellschaft zur Foerderung der Angewandten Forschung E.V., Munich (DE)

(72) Inventors: Michael Krause, Halle (DE); Thomas Hoeche, Halle (DE)

(73) Assignee: FRAUNHOFER-GESELLSCHAFT ZUR FOERDERUNG DER ANGEWANDTEN FORSCHUNG E.V. (DE)

( * ) Notice: Subject to any disclaimer, the term of this patent is extended or adjusted under 35 U.S.C. 154(b) by 0 days.

(21) Appl. No.: 14/243,354

(22) Filed: Apr. 2, 2014

(65) Prior Publication Data

US 2014/0299785 A1  Oct. 9, 2014

(30) Foreign Application Priority Data

Apr. 4, 2013  (EP) .................................. 13162360

(51) Int. Cl.

| | |
|---|---|
| *B44C 1/22* | (2006.01) |
| *C03C 15/00* | (2006.01) |
| *C03C 25/68* | (2006.01) |
| *C23F 1/00* | (2006.01) |
| *B23K 26/364* | (2014.01) |
| *B23K 26/02* | (2014.01) |
| *B23K 26/035* | (2014.01) |
| *G01N 1/04* | (2006.01) |
| *B23K 26/38* | (2014.01) |
| *G01N 1/28* | (2006.01) |
| *G01N 1/32* | (2006.01) |
| *G01N 1/00* | (2006.01) |

(52) U.S. Cl.
CPC ................ *B23K 26/38* (2013.01); *G01N 1/00* (2013.01); *G01N 1/286* (2013.01); *G01N 1/32* (2013.01); *G01N 2001/2886* (2013.01); *H01J 2237/31745* (2013.01)

(58) Field of Classification Search
CPC .. B23K 26/02; B23K 26/035; B23K 26/364; G01N 2001/045
USPC ..................................................... 216/65, 66
See application file for complete search history.

(56) References Cited

U.S. PATENT DOCUMENTS

| | | | | |
|---|---|---|---|---|
| 2004/0164242 A1* | 8/2004 | Grunewald | ............... | G01N 1/32 250/307 |
| 2008/0042058 A1* | 2/2008 | Schampers et al. | .......... | 250/307 |
| 2011/0017922 A1* | 1/2011 | Amador | .................. | H01J 37/20 250/442.11 |
| 2011/0250734 A1* | 10/2011 | Choi et al. | .................... | 438/463 |

\* cited by examiner

*Primary Examiner* — Thomas Pham

(74) *Attorney, Agent, or Firm* — Gesmer Updegrove LLP

(57) ABSTRACT

Method for manufacturing a sample for microstructural materials diagnostics, especially for transmission electron microscopy examinations, for scanning electron microscopy examinations for transmission electron-backscatter diffraction, for Rutheford backscatter diffraction, for elastic recoil detection analysis, for X-ray absorption spectroscopy or for X-ray diffraction, comprising detaching a basic structure from a preferably flat substrate by irradiating the substrate with a high energy beam, preferably with a laser beam, wherein the basic structure comprises a supported structure being supported by a supporting structure, preferably a cantilever beam which is supported at least at one of its both ends, preferably at both of its ends, by the supporting structure, the supporting structure being configured to be held by a jig, preferably to be clamped in the jig, and thinning the supported structure at least in sections by cutting, preferably by grazing, its surface, preferably at least at one of its lateral faces and/or of its front faces, preferably two opposing ones of its lateral faces, with the high energy beam.

18 Claims, 9 Drawing Sheets

Figure 1:
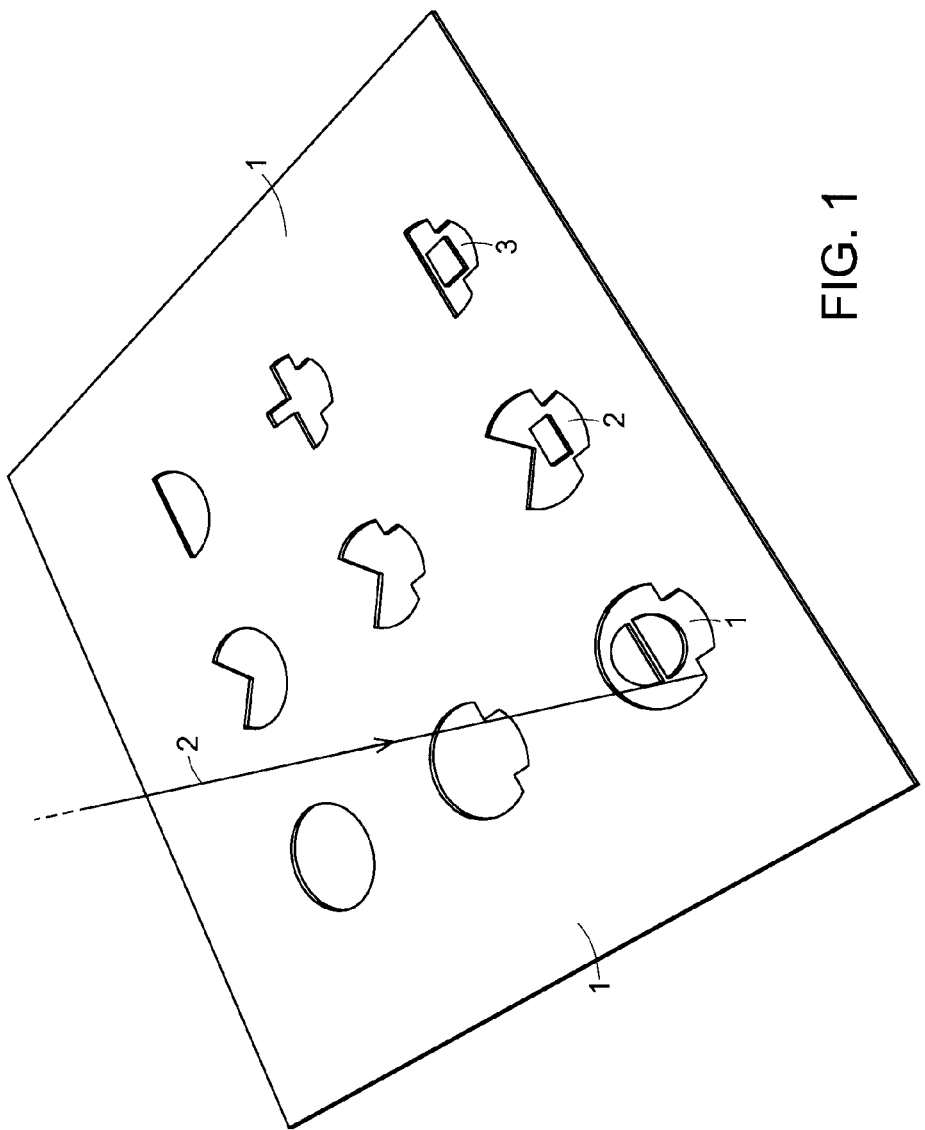

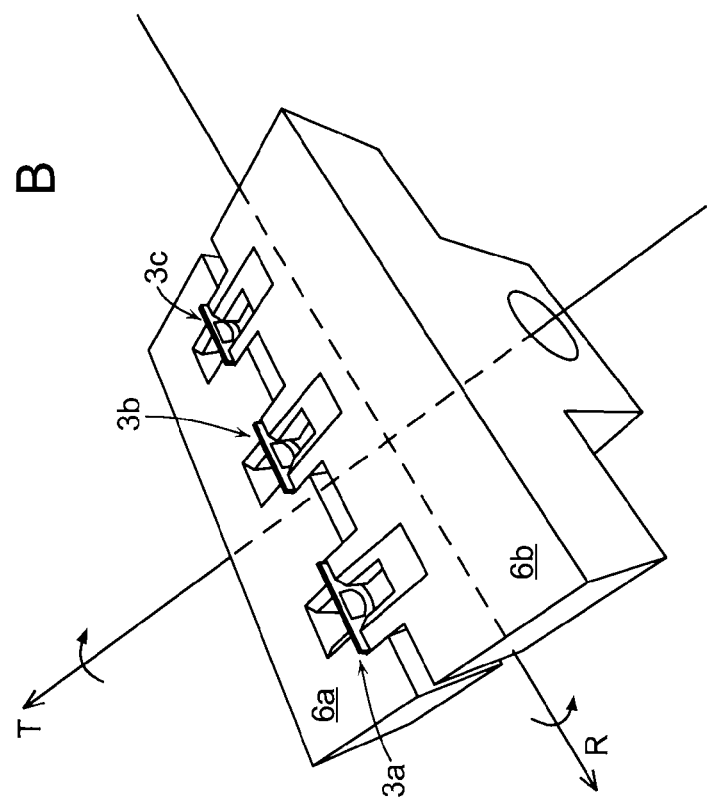
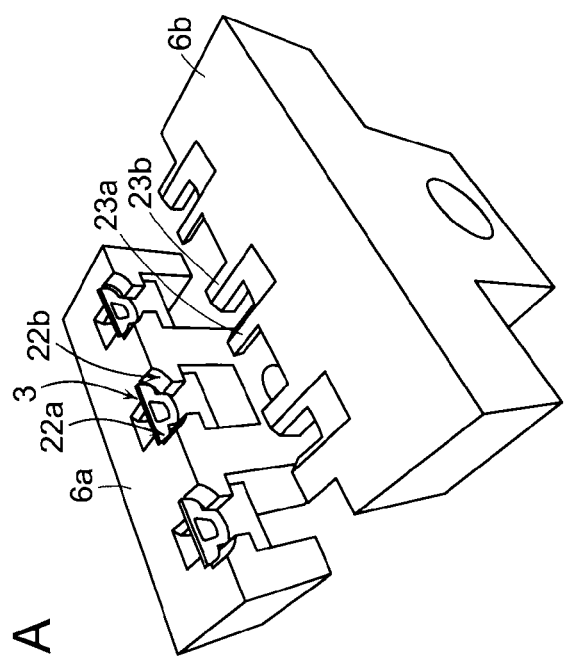
FIG. 3

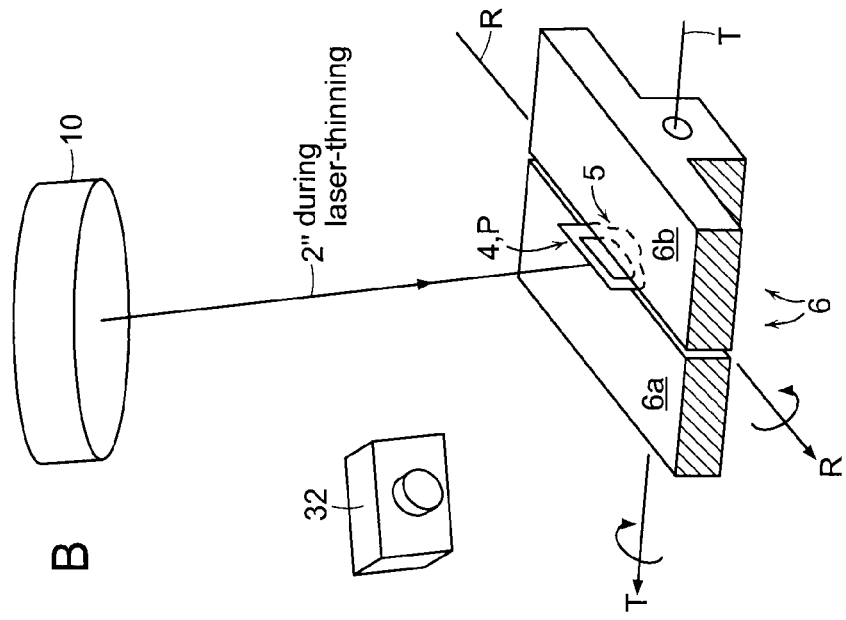
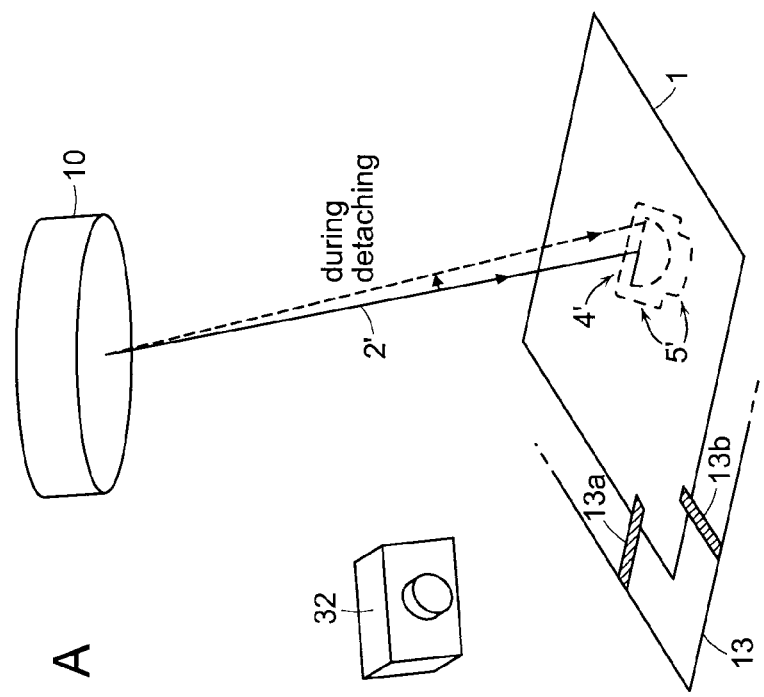
FIG. 8

METHOD AND ARRANGEMENT FOR MANUFACTURING A SAMPLE FOR MICROSTRUCTURAL MATERIALS DIAGNOSTICS AND CORRESPONDING SAMPLE

PRIORITY INFORMATION

This application claims priority to EP Application No. 13162360.5 filed on Apr. 4, 2013, which is incorporated herein by reference in its entirety.

BACKGROUND OF THE INVENTION

The present invention relates to a method for manufacturing a sample for microstructural materials diagnostics, especially for transmission electron microscopy (TEM) examinations, for scanning electron microscopy (SEM) examinations, for transmission electron-backscatter diffraction, for Rutherford backscatter diffraction, for elastic recoil detection analysis, for X-ray absorption spectroscopy or for X-ray diffraction.

Methods in this technical field are known from the applications DE 10 2011 111 190 A1 and EP 2 413 126 A2. The known methods, however, require expensive equipments in order to realize the methods in practice. Especially, the method in DE 10 2011 111 190 A1 needs a specific and expensive optics in order to trepan grooves into a plate-shaped substrate for preparing the sample for microstructural materials diagnostics. Also, the reliability of the optics to be used according to the known methods is restricted. Thus, the stability of the manufactured samples cannot be guaranteed in each case. Furthermore, in the equipments known from the prior art to realize the sample manufacturing, complicated adjustments are necessary and long-term stability of the optical adjustment is an issue.

SUMMARY OF THE INVENTION

It is therefore the objective of the present invention to provide an alternative method for manufacturing a sample for microstructural materials diagnostics, which can be realized in practice with a reliable, less expensive equipment and which allows the manufacturing of the sample with an improved, high reliability and reproducibility. A further objective of the invention is to provide a corresponding arrangement for manufacturing a sample for microstructural materials diagnostics and to provide corresponding samples.

This objective is solved by the method according to claim 1, the arrangement according to claim 12 and the samples according to claims 16 and 17. Advantageous features of said method, arrangement and samples are described in the dependent claims.

Hereinafter, the present invention is at first described in a general way. Afterwards, embodiments of the invention are described which show examples how the present invention can be realized in detail. However, it is not necessary to realize the present invention (according to the independent claims) as is described in the specific embodiments: Especially, features shown in the embodiments can be omitted or also combined with other features shown in other embodiments in a manner which is not explicitly shown in the annexed embodiments. Also, single features shown in the embodiments can already improve the state of the art on their own (i.e. without the other features shown in the embodiments).

A method according to the invention is described in claim 1.

According to the invention, the detached basic structure comprises both the supported structure and the supporting structure. In other words, in general, the supported structure as well as the supporting structure are both integral parts of the (detached) basic structure, i.e. in general, the supported structure and the supporting structure are configured as one piece (the latter being denoted as basic structure).

The supporting structure is configured to be firmly held by a jig for thinning the supported structure. Hereinafter, the expression of mount or of clamp is used as a synonym (i.e. alternatively) for the expression of jig. However, both expressions have the same meaning.

The method is especially employed for manufacturing a sample for transmission electron microscopy examinations, for scanning electron microscopy, for transmission electron-backscatter diffraction, for Rutherford backscatter diffraction, for elastic recoil detection analysis, for X-ray absorption spectroscopy, or for X-ray diffraction.

Preferably, the supported structure is a bar, this bar alternatively being denoted as beam hereinafter. This bar can be a cantilever beam which is supported at least at one of its ends, preferably at both of its ends, by the supporting structure. The holding of the supporting structure by the jig for performing a laser-based thinning of the supported structure is preferably a clamping of the supporting structure in the jig. The thinning of the supported structure at least in sections by cutting its surface is preferably performed by grazing its surface. Therein, preferably, at least one of the lateral faces and/or of the front faces, preferably two opposing ones of the lateral faces, of the surface of the supported structure are cut (preferably: grazed) with the laser beam. Alternatively, the laser beam used in the detaching and in the thinning step is denoted as high-energy beam hereinafter.

The substrate can be an essentially flat substrate (for example a wafer-shaped substrate). However, in principle also the processing of a non-flat, essentially arbitrarily shaped substrate is feasible. The detaching (to be performed prior to the subsequent thinning) means that the basic structure (i.e. the geometry thereof) is cut out of, by means of the high-energy-beam based cutting process in form of a laser-cutting process, the substrate. The supported structure (especially the cantilever beam) resulting from this detaching or cutting out preferably is an elongated body with (seen perpendicular to its longitudinal axis) preferably rectangular or trapezoid cross-section. However, other non-elongated shapes of the supported structure (especially of the cantilever beam) are possible.

Figure 7:
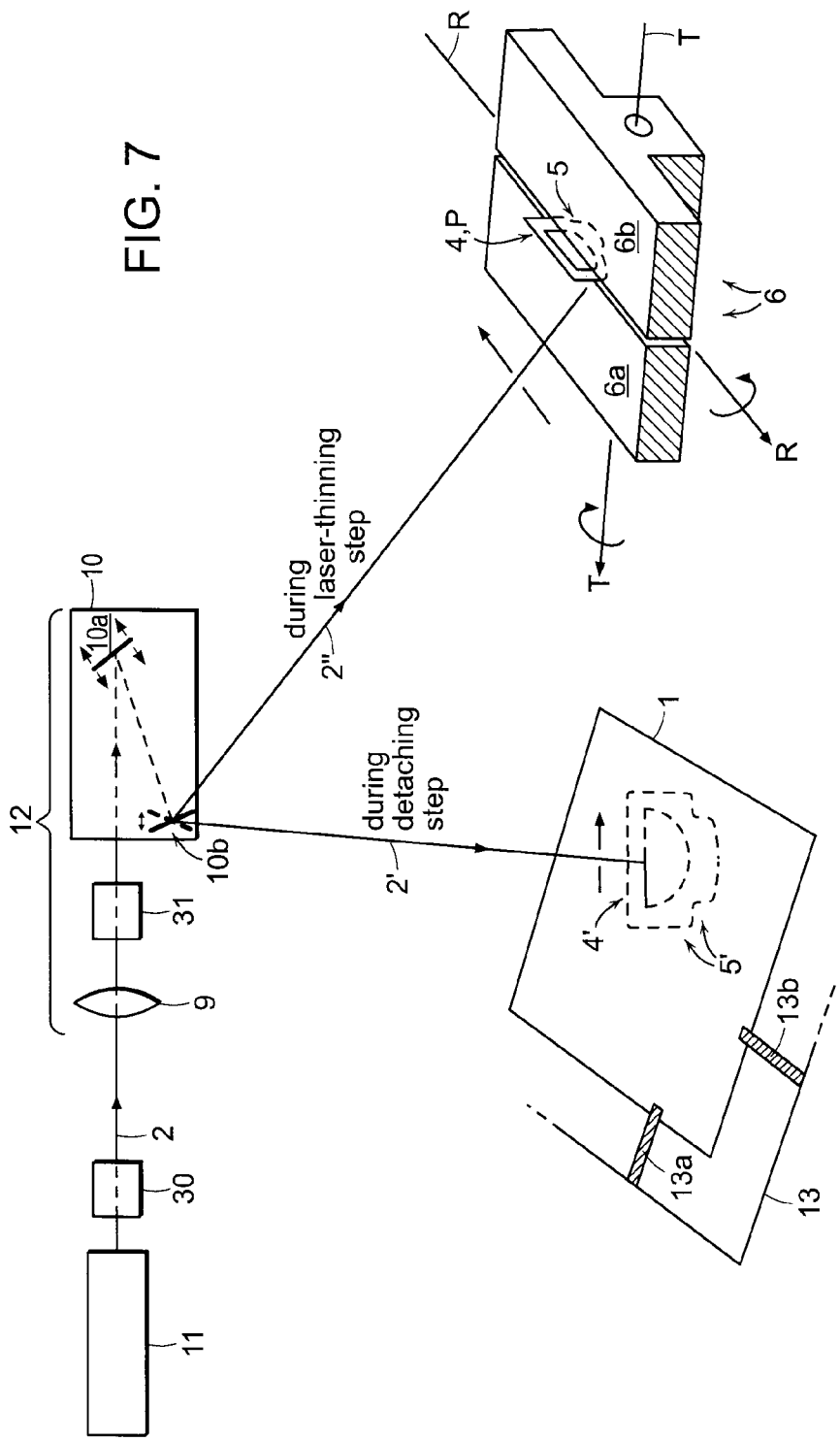

In the detaching step, a (preferably elongated) body is prepared as the supported structure (preferably: the cantilever beam) by removing substrate material over the whole circumference of the body. Normally, the supported structure is connected with the supporting structure in such a manner that these two structures are made of the same material and form two parts of one and the same single piece. Preferably, the cantilever beam is only connected to the supporting structure at (seen along its longitudinal axis) at least one of its two ends. The detached basic structure comprises the supported structure (preferably: the cantilever beam) and the supporting structure supporting this supported structure by connecting with the latter. In other words:

If the supporting structure of the basic structure is held, preferably clamped, by the jig during the subsequent thinning step, also the supported structure (for example the cantilever beam) which is fixed to the basic structure is immovably seized by the jig. (During the laser processing for detaching the basic structure, the flat substrate is normally not held by the jig which is used during the thinning step: As can be seen in FIG. 7, a second jig is normally used for holding the substrate during the laser processing for detaching. Having detached the basic structure, this structure is then moved from the second jig to the jig which will be used during the thinning step and clamped in this jig before the thinning starts.)

Thus, in general, the basic structure is a self-contained, integral structure which comprises the supported structure and the supporting structure, wherein the supported structure is integrally connected with the supporting structure (both are machined out of the same workpiece) and wherein the supporting structure is configured to be held by the jig Hereinafter, the holding of the supporting structure in or by the jig (or mount) is described in an exemplary way by a jig (mount) clamping the supporting structure for the thinning of the supported structure. This is however not limiting: Instead of clamping the supporting structure, one can also glue the supporting structure on the jig, one can glue the supporting structure on a substrate to be sacrificed (which can then be clamped by the jig) or one can suck the supporting structure with and/or onto the jig (by means of a partial vacuum or a vacuum) in order to hold the supporting structure by the jig. The supporting structure is therefore held by the external jig and in turn holds the supported structure. This confers stability to the supported structure which is extremely fragile after the laser thinning.

In the thinning step after the detaching step (which is also denoted as high-energy beam based thinning in form of laser-based thinning hereinafter), at least parts of the rim of the supported structure, preferably of the cantilever beam (i.e. at least parts of its outside surface between its two ends) are laser-processed by irradiating the laser beam, in such a manner onto the outer surface of the supported structure, preferably of the cantilever beam, that this beam cuts into this outer surface. Preferably, the laser beam is irradiated in a grazing manner onto the outer surface of the supported structure, preferably of the cantilever beam (see definition of grazing incidence hereinafter).

Hereinafter, the present invention is further described with the non-limiting example of a bar and cantilever beam, resp., as the supported structure.

Grazing incidence of the laser beam onto the cantilever beam means that the laser beam is irradiated onto a surface area of the cantilever beam in a manner essentially parallel to this surface area and in such a manner that a material removal takes place which extends from the surface up to a predefined depth in the material of the cantilever beam below the surface. Essentially parallel means that there is a maximum inclination angle, between this surface area (or the tangent to this surface area, respectively) and the direction of incidence of the laser beam, of about ±15°. Without limiting the scope of the claims, the thinning of the supported structure by cutting into its surface is described hereinafter based on the said grazing incidence.

As the high-energy-beam a laser beam is used. The laser beam can have a power of between 1 W and 50 W directly at the laser's output side. In general, for the detaching step and for the subsequent thinning step, the same laser (preferably with different output power) is used. However, also two different lasers can be used for these two steps.

In the thinning step, normally, the lateral faces of the cantilever beam are laser-processed by grazing them with the laser beam. The lateral faces of the cantilever beam are those faces of the beam which are arranged in parallel to the plane of the substrate from which the basic structure with the cantilever beam is detached. Therefore, normally, the laser beam is irradiated onto the cantilever beam essentially parallel to the plane of the substrate. However, in principle, it is also possible to thin the cantilever beam perpendicular to the substrate plane, i.e. to thin the front faces of the cantilever beam. The front faces are the faces which are perpendicular to the lateral faces (if, during the detaching step, the laser beam is irradiated vertically onto the substrate), i.e. are those faces which are generated during the detachment of the basic structure from the substrate. In order to graze the front faces of the cantilever beam, the laser beam has to be directed, during the thinning step, vertically onto the substrate's plane of the cantilever beam. The substrate's plane of the cantilever beam is the plane of the basic structure which corresponds to the plane of the substrate before detachment of the basic structure.

The basic structure to be detached may correspond to an essentially circular or semi-circular disc, which can be segmented during the detaching step by introducing holes, geometric zones, etches, etc. in order to carve out the structure of the cantilever beam (and also structures which guarantee an optimum clamping by the mount). In other words: The laser-processing during the detaching step is performed in a manner which optimizes the basic structure for the subsequent laser-processing during the laser-based thinning step.

In general, however, the structures to be introduced into the cantilever beam by the grazing incidence of the laser beam do not have to be introduced essentially in parallel to the lateral faces and/or to the front faces of the cantilever beam. It is also possible to rotate, preferably to continuously toggle the cantilever beam (and the clamped basic structure) within a certain range of angles, by rotating the mount in order to reduce curtaining effects imposed by the high-energy-beam based processing (for example the laser beam based micro-machining).

Moreover, the two-stage laser process according to the invention facilitates a precise adjustment of the height of the supported structure. This allows the preparation of more rugged or more suitable-for-laser-thinning supported structures than ever imaginable. For example the bar (beam) don't even has to be a cuboid structure but could for example resemble an arch bridge or alike.

First advantageous features of the method according to the invention are described in claim 2. (These features can be combined with further advantageous features of further dependent claims mentioned below in an arbitrary manner in accordance with the claim structure.)

Second advantageous features of the method according to the invention are described in claim 3. Thus, in order to further thin the already thinned sections of the cantilever beam, it is preferred to realize the steps described in dependent claim 2 and/or in dependent claim 3.

After irradiating the already thinned sections with the ion beam with a glancing angle $\beta$ (hereinafter also denoted as tilt angle $\beta$) of $\beta>0°$, a wedge-shaped rest remains from the sections already thinned by the laser-based thinning, which rest advantageously has a thickness between 10 and 100 nm, preferably between 30 and 80 nm, in an area around the tip of the wedge. This remaining rest can then be used as a lamella-sample for microstructural materials diagnostics according to the present invention (especially as a transmission electron microscopy lamella sample).

According to claims 2 and 3, therefore, the ion beam is irradiated essentially parallel (except for the tilt angle $\beta$) along the longitudinal direction of a/the channel structure(s) introduced into the lateral face(s) of the cantilever beam during the laser-based thinning in order to further thin the wall structures remaining between laser-introduced channels at their thinnest areas.

The ion beam can be emitted by a heavy duty ion beam source. This source can be a HF or ECR source operated between 500 eV and 50 keV. The ion beam can have a primary ion-dose density of between $10^{13}$ cm$^{-2}$ and $10^{22}$ cm$^{-2}$ directly at the source's output side. Also, a plasma jet emitted by a plasma source can be used in order to generate the ion-beam. This source can be an atmospheric plasma jet source. The plasma jet can have a primary ion-dose density of between $10^{13}$ cm$^{-2}$ and $10^{22}$ cm$^{-2}$ directly at the source's output side.

The ion beam can be irradiated essentially parallel (except for the tilt angle β) along the longitudinal direction of a/the channel structure(s) introduced into the lateral face(s) of the cantilever beam such that the direction of incidence of the ion-beam faces from a side of the cantilever beam on which the cantilever beam is not tapered to a side of the cantilever beam on which the cantilever beam is tapered.

It is also possible to realize the ion-beam based thinning-postprocessing simultaneously on both opposing lateral faces of the already thinned supported structure by using two ion beams.

As already said, the substrate's plane of the cantilever beam corresponds to the former plane of the substrate before cutting off the basic structure. This plane can be an arbitrary plane parallel to the two opposing surfaces of the substrate and lying in between these surfaces. However, in the following, the plane which is arranged exactly in the middle between these two opposing, parallel surfaces of the substrate is used as the substrate's plane of the cantilever beam (and the plane of the substrate, respectively). Compare the plane shown in a dashed manner in FIGS. 6b and 6c.

In claim 4, the broadening angle 2α is the angle of the beam extension when the laser beam is impinging on the cantilever beam.

Preferably, the cantilever beam is thinned on the two opposing lateral faces at identical positions (seen along the longitudinal extension of the cantilever beam) by grazing these two surfaces of the cantilever beam with the laser beam in a direction parallel to the substrate's plane of the cantilever beam. In order to realize this, it is possible to use a beam splitter which splits the laser beam, before it impinges on the cantilever beam, into two partial beams. This has the advantage that both of the lateral faces of the cantilever beam can be processed simultaneously.

On the other hand, as described in further detail in the embodiments below, it can be advantageous to tilt the main beam axis of the laser beam relative to the substrate's plane of the cantilever beam by the angle α as follows: During the processing of the first lateral face, a predefined angle α is used in order to balance the angular extension of the laser beam when impinging on the cantilever beam (so that the thinning can be performed parallel to the processed lateral face). Before processing the second one of the two opposing lateral faces, the cantilever beam (and the substrate's plane of it, respectively) is tilted, relative to the laser beam, in the opposite direction by the angle of 2α. This means that, again, there is a tilt angle α between the main beam axis of the laser beam and the substrate's plane of the cantilever beam, so that also a parallel thinning of the second one of the two opposing lateral faces is possible (compare description of FIG. 5B hereinafter).

Further advantageous features are described in claim 5.

Again, in claim 5, the surfaces of the cantilever beam to be thinned are preferably lateral faces thereof. The channel structures introduced into these surfaces by grazing the surfaces with the laser beam preferably have (in the preferable alignment described in claim 3) the shape of a circle segment or of an elliptical segment (seen in a cross-section perpendicular to the substrate's plane of the cantilever beam and perpendicular to the longitudinal direction of the channel structures).

Instead of aligning the channel structures perpendicular to the longitudinal extension of the supported structure (cantilever beam), the channel structures can also be introduced with a different angle relative to the supported structure. Especially, different channel structures can be introduced with different angles relative to the supported structure. For example, on the two opposing lateral faces of the supported structure, two channel structures which cross (or intersect) each other can be introduced as is described in DE 10 2011 111 190 A1.

Further advantageous features are described in claim 6.

It is therefore, according to claim 6, preferred to introduce on both sides of the cantilever beam (i.e. into the two opposing lateral faces) several channel structures in such a way that, for each single introduced channel, the wall section of the channel facing the substrate's plane of the cantilever beam is remaining in form of a thinned division bar (hereinafter also denoted as remaining section). The division bar remains between two channels introduced symmetrically on opposite (lateral) sides of the cantilever beam (symmetrically with respect to the substrate's plane of the cantilever beam). The division bar and remaining section, respectively, may have (seen perpendicular to the substrate's plane of the cantilever beam) a thickness of some micrometers (microns) or some 10 micrometers.

Further advantageous features are described in dependent claim 7.

According to the first alternative of claim 7, channel end supports remain at one of the two ends (seen in the longitudinal direction of the respective channel structure) of some of the channel structures. Preferably, those channel structures which are provided with such channel end supports (in order to increase the stability of the thinned cantilever beam) are the channel structures adjacent to the ends of the cantilever beam. It is possible to realize different channel structures with different extensions (along the longitudinal direction of the respective channel structure) of their channel end supports, i.e. with different depths of the channel structures. It is preferred to let the extension of the channel end support decrease (with a corresponding increase of the depths of the channel structures) from the outer boundaries of the thinned section of the cantilever beam to the centre thereof (i.e. seen from both of the ends of the cantilever beam to the centre of the cantilever beam if the thinned sections are introduced in a symmetrical manner with respect to this centre).

According to the second alternative described in claim 7, it is preferred that the front faces (that means generally the narrow sides) of the cantilever beam are arranged, by vertically irradiating the substrate in the detaching step, perpendicular to the substrate's plane of the cantilever beam and therefore perpendicular to the lateral faces in which the several channel structures are introduced. Emanating means starting from a surface of the cantilever beam and being introduced, by laser-based material removal, into a predefined depth of the cantilever beam material.

Further advantageous features of the claimed method are described in claim 8, wherein, advantageously, all mentioned features are realized. Using a material thickness of the substrate of, for example, 100 micrometer or 150 micrometer (which is the material thickness the laser beam has to cut and, by the way, which is the maximum thickness accommodated by conventional sample supports used in transmission electron microscopy examinations) has the advantage that lasers with relatively small mean output power can be used. After the detaching step, the substrate can be clamped in a mount and can be fixed with a screw prior to thinning of the supported structure. Also other mounts can be used to clamp the substrate after the detaching step (such mounts are well-known to a skilled person).

Further advantageous features are described in the dependent claims 9 and 10.

For the laser-processing in the detaching as well as in the thinning step of the present invention, femto- or picosecond lasers (as well as nanosecond lasers) can be used. These lasers only have a heat-effective zone of at most some micrometers (for the nanosecond lasers; for the femto- or picosecond lasers, the heat-effective zone has at most a size of some 100 nm). Types of lasers and wavelengths which are used advantageously can be diode pumped solid state Nd:YAG lasers emitting at 1064 nm, frequency doubled at 532 nm or frequency tripled at 355 nm, or Ti:Saphire lasers emitting at approx. 775 nm to 800 nm, or $YVO_4$ laser emitting at 1030 nm, 515 nm (doubled) or 343 nm (tripled).

The fluence of the laser (at the location of impingement on the substrate and the cantilever beam, respectively) is advantageously above the ablation threshold of the material to be machined, for example between 0.1 $J/cm^2$ and 1 $J/cm^2$.

According to the second aspect of claim 10, the basic structure can be toggled around the said second axis (compare also FIG. 3) in order to reduce or avoid undesired curtaining effects.

In accordance with the second aspect of claim 10, in order to hold (or clamp) the supporting structure of the basic structure by the jig, the jig (hereinafter also denoted as clamp) can have two clamping jaws configured to clamp the supporting structure (or parts thereof) in-between. To guarantee a reliable and immovable fixing of the basic structure relative to the clamp and in the clamp, i.e. to fix, the basic structure in a defined position relative to the clamp, the basic structure can be provided with at least one, preferably at least two notch(es) in its supporting structure. The clamping jaws can then be provided with at least one, preferably at least two corresponding engagement section(s) to be engaged with the notch(es). The notch(es) can be introduced by realizing an appropriate shape of the basic structure and the supporting structure, respectively, based on an adequate moving of the laser beam across the surface of the substrate during the detaching step.

According to the present invention, in order to realize an optimized laser-based material removal from the cantilever beam (in order to realize the shape of the thinned sections in exactly the desired manner), it is advantageous to use, according to both aspects of the dependent claim 10, the described mount to clamp, fix, and position the basic structure with its supporting structure and cantilever beam relative to the processing laser beam, which is generated and moved with a beam-forming device (especially: an optical device) comprising a focusing optics and a beam deflector (for example a galvanometer scanner), see claim 10, in order to realize the desired grazing incidence of the laser beam onto the cantilever beam with high precision.

According to the preferable aspects of claim 11, the holding frame is an already detached part of the substrate or corresponds to the substrate. The holding frame encloses the not yet fully detached basic structure. Preferably, the holding base(s) connect(s) the holding frame with the basic structure at the side of the supported structure and adjacent to the supported structure, but nevertheless part of the supporting structure is connected via the holding base(s) to the holding frame.

All this can be done in an arrangement according to claim 12.

Therein, preferably, the beam-forming device comprises a focusing optics and beam deflector. The pose is defined as the position and the orientation of the basic structure (with its supporting structure and cantilever beam).

The focusing optics can be realized as so-called Varioscan, i.e. the optics comprises a focusing lens which can be adjusted with a very high velocity in the direction of the beam (based on a coil). This way, a movement of the sample in order to focus the beam properly becomes superfluous.

The jig preferably holds the supporting structure in such a manner that the high-energy-beam can cut into the surface of the supported structure which is to be processed in an unobstructed manner and/or in such a manner that any re-deposition of material is avoided.

Advantageous features of the arrangement according to the invention are described in claims 13 to 15.

According to claim 13, after the laser-beam-based thinning, the detached basic structure with its supporting structure and its already thinned supported structure can be removed from the jig (for the purpose of thinning the supported structure with the laser beam) and afterwards be positioned in an ion-beam based etching system configured to perform the thinning-postprocessing for further thinning.

Furthermore, also at least one beam-shaping element can be introduced into the path of the high energy beam. With this beam-shaping element, the cross section of the beam can be shaped in a desired manner before the beam impinges onto the supported structure to be processed.

For example a cylindrical lens in order to elliptically shape the beam cross section for introducing elongated (seen in the direction of the longitudinal extension of the supported structure) channel structures such as elongated holes can be introduced into the ray path of the high energy beam.

In addition (or alternatively), also at least one of the following beam shaping elements can be introduced into the path of the high-energy beam:
- A diffraction element to alter the cross section of the (circular) beam into preferably a rectangular or quadratic shape and/or
- an element which changes a Gaussian-shaped profile of the beam into a flat-top shape.

Also, at least one beam splitter can be introduced into the path of the high energy beam in such a manner that the resulting (for example: two) partial beams can be directed onto the two opposing lateral faces of the supported structure in order to simultaneously introduce channel structures into these two faces.

Preferably, the laser to be used as the beam-emitting unit can be an ultra-short pulsed laser which generates ultra-short laser pulses (i.e. ps-pulses or fs-pulses). However, in principle (even if not preferred due to the larger heat affected zone being generated in the processed material of the supported structure), also a short-pulsed laser generating short laser pulses (i.e. ns-pulses) can be used.

A sample for microstructural materials diagnostics according to the invention is described in claims 16 to 18.

Especially, in a structure according to claim 16 which has been produced in accordance with dependent claim 2, the thinning with a laser beam and the subsequent ion based post-thinning of the already thinned sections are performed with one and the same structure, namely with the supported structure.

In accordance with claims 17 and 18, the sample can also be a supporting structure in form of a half-ring on which a cantilever beam (as the supported structure) is mounted.

Compared to the methods and arrangements known from the prior art, the present method and arrangement for manufacturing a sample for microstructural materials diagnostics especially have the following advantages.

Due to the specific shape of the basic structure comprising the supporting structure as well as the cantilever beam (the latter forming the basis for the finally resulting sample due to the thinning and, if necessary, the thinning-post processing) and being detached in the detaching step of the invention, no separate holding structure for mounting the sample in a sample holder (for example a half ring for mounting/ gluing etc.) during the microstructural materials diagnostics is necessary because the supporting structure can serve for this purpose itself.

Nearly arbitrary shapes for the basic structure (and therefore for the supporting structure as well as the cantilever beam) to be detached can be realized. Details of the contour of the basic structure can be transferred directly as CAD-based trajectory to the laser-processing parts of the arrangement. Finite element methods can be used in order to estimate the stability of the cantilever beam (while already considering the local thinning during the laser-based thinning step of the present invention). Due to the combination of the supporting structure and the cantilever beam in one single basic structure, a secure manipulation with a pair of tweezers can be guaranteed. The only geometric restrictions of the shape of the basic structure result from the diameter of the used laser beam (for example approximately 10 micrometers), the precision to position the laser beam (<1 micrometer) and, dependent upon the used laser source, the size of the introduced damage zone.

The manufacturing of the preferably flat substrate to be used in the detaching step can be easily performed by mechanical preparation steps (for example: high precision sawing, plane-parallel grinding, or the like). Using the substrate with a thickness of approximately 100 to 150 micrometers (and not for example with a thickness of 300 to 500 micrometers which is necessary in the state of the art in order to realize sufficient stability) makes it possible to use laser types with small mean output power, which reduces costs (a thickness of 300 to 500 micrometers can be realized as width of the supported structure with the present invention).

The detaching and the thinning step of the present invention can be realized based on a mechanical clamping and on a precise positioning (for example by deflection with a beam deflector, especially a galvanometer scanner) of a laser beam. Thus, expensive drilling and/or moving systems for the processing of the substrate are not necessary.

Beyond that, the laser system used in the invention also allows to label the basic structure (or the supporting structure thereof). This improves the traceability of samples. Also, additional structures (such as the mentioned notches) can be introduced easily, which allow an easy handling or clamping of the basic structure in the used mount.

It is also possible to process cross-sectional samples (for example cross sections which have been realized based on sandwiches formed by layered coatings on thin substrates) as substrates in the present invention. Arbitrary orientations of the basic structure (and therefore also the cantilever beam to be examined during the microstructural materials diagnostics) can be realized.

DETAILED DESCRIPTION OF THE ILLUSTRATED EMBODIMENTS

Hereinafter, specific embodiments and features of the invention are described with respect to FIGS. 1 to 8.

Therein, the following is shown:

FIG. 1: A substrate irradiation and detachment (partly) of a desired basic structure.

Figure 2:
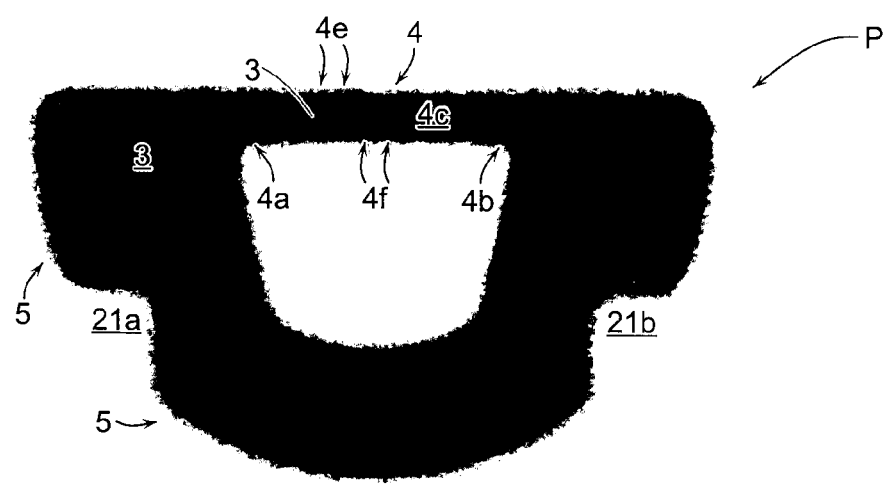

FIG. 2: A detached basic structure before the subsequent laser-based thinning.

Figure 2A:
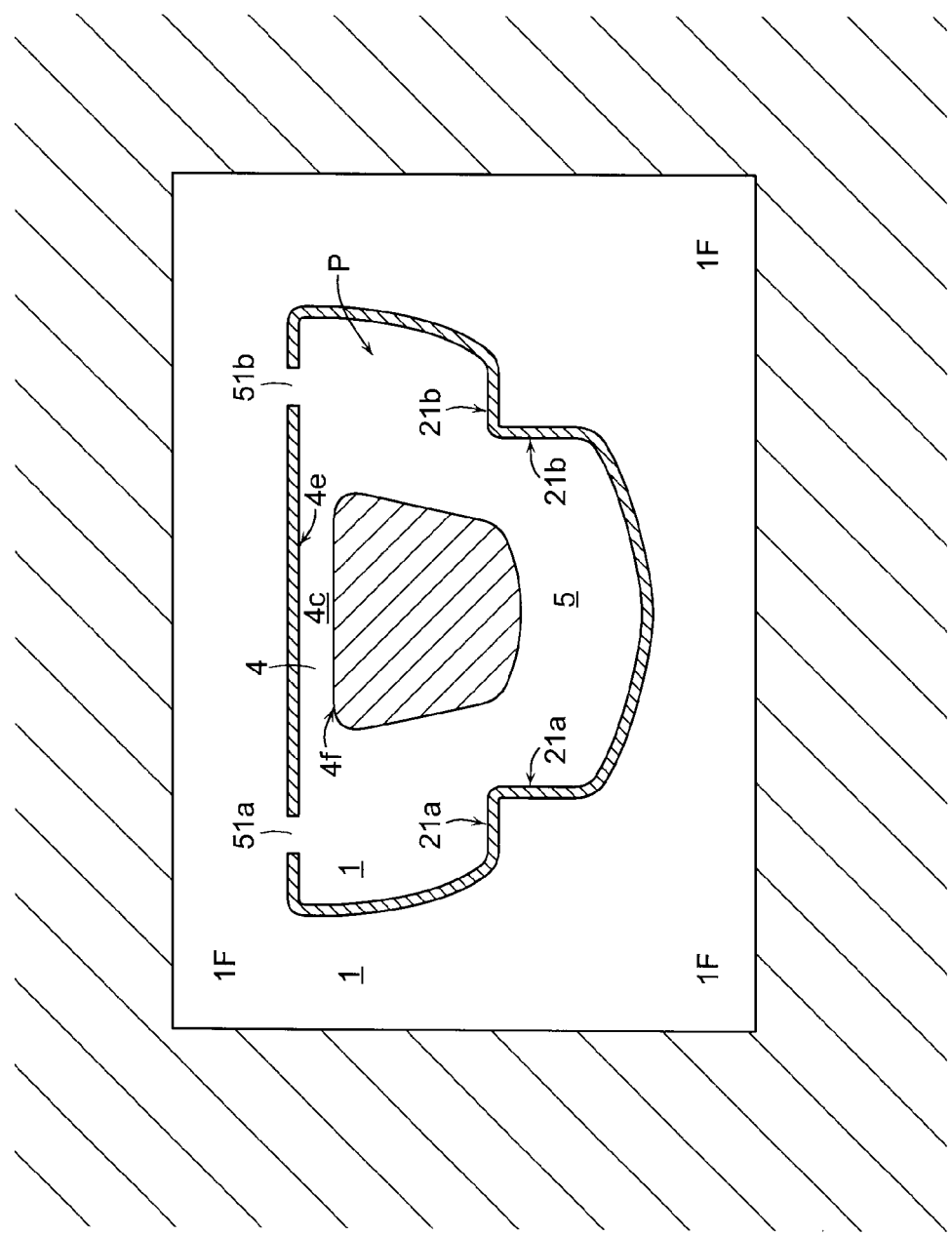

FIG. 2a: A sketch of the to-be-detached basic structure of FIG. 2.

FIG. 3: A mount which can be used during the laser-based thinning.

Figure 4:
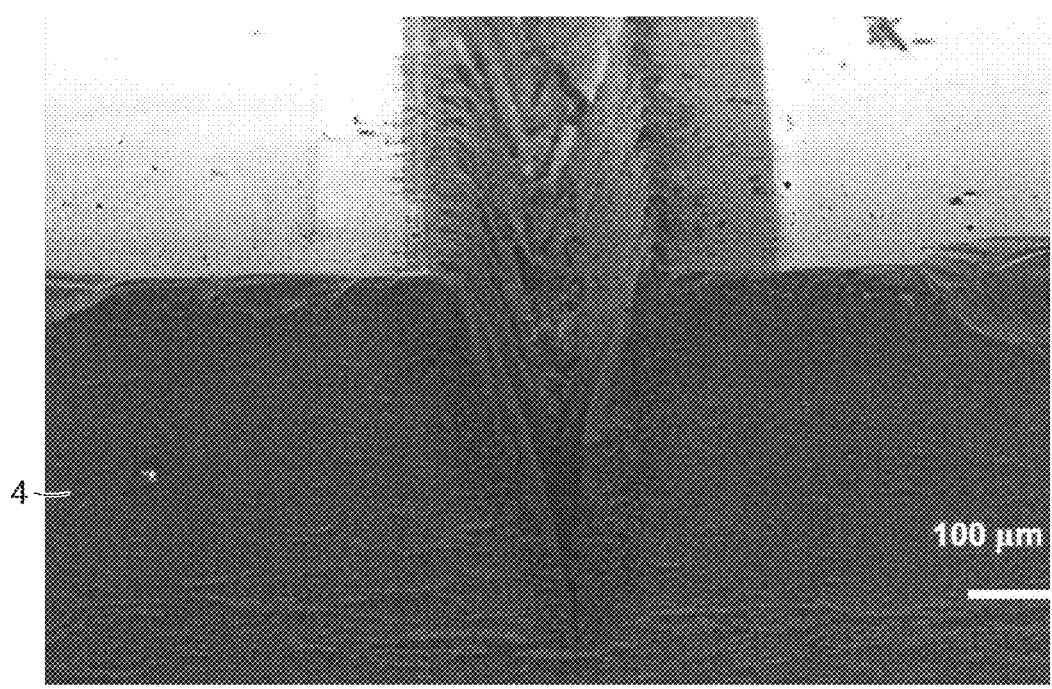

FIG. 4: A groove introduced into the material of a substrate in accordance with the laser-based thinning step of the invention.

Figure 5:
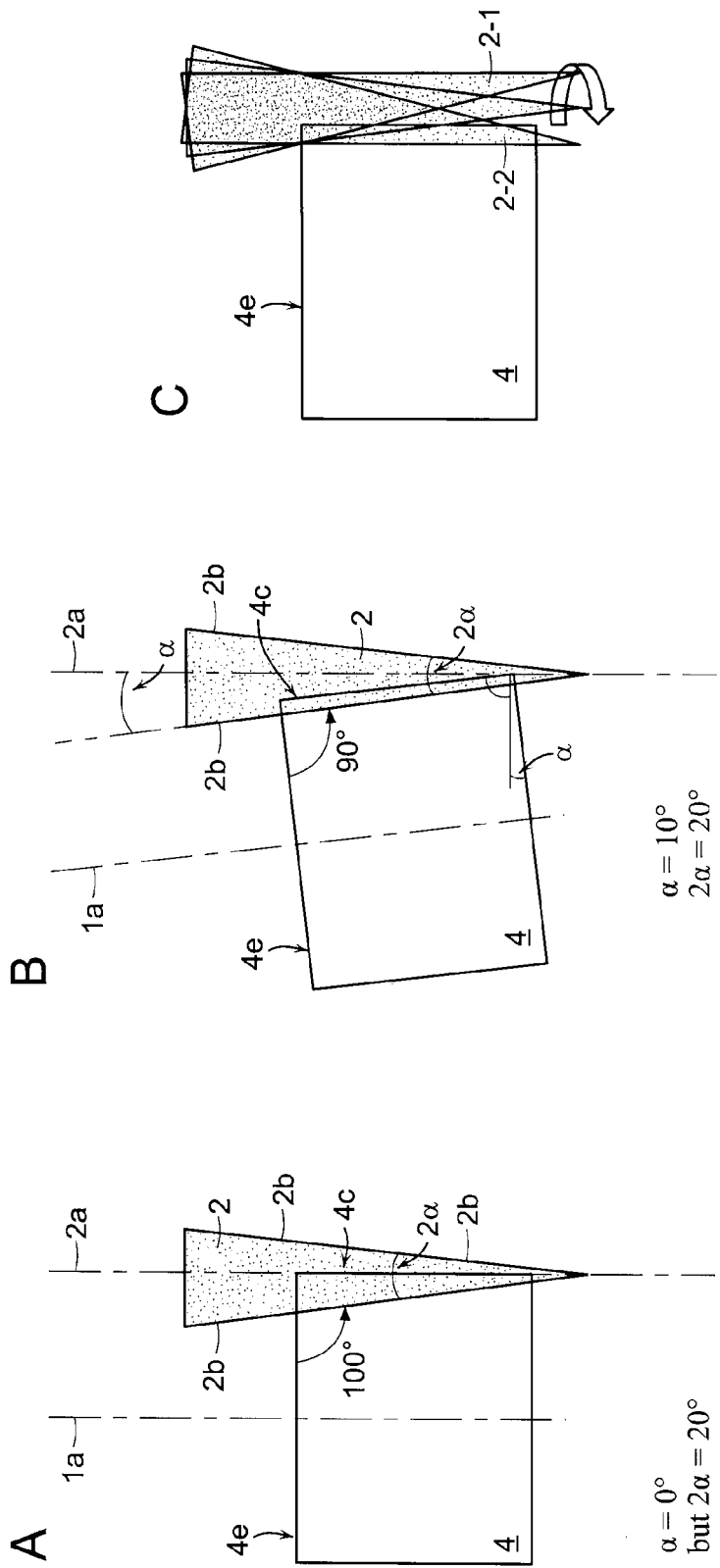

FIG. 5: An explanation of how to realize perpendicular channel structures in the cantilever beam during the laser-based thinning step.

Figure 6:
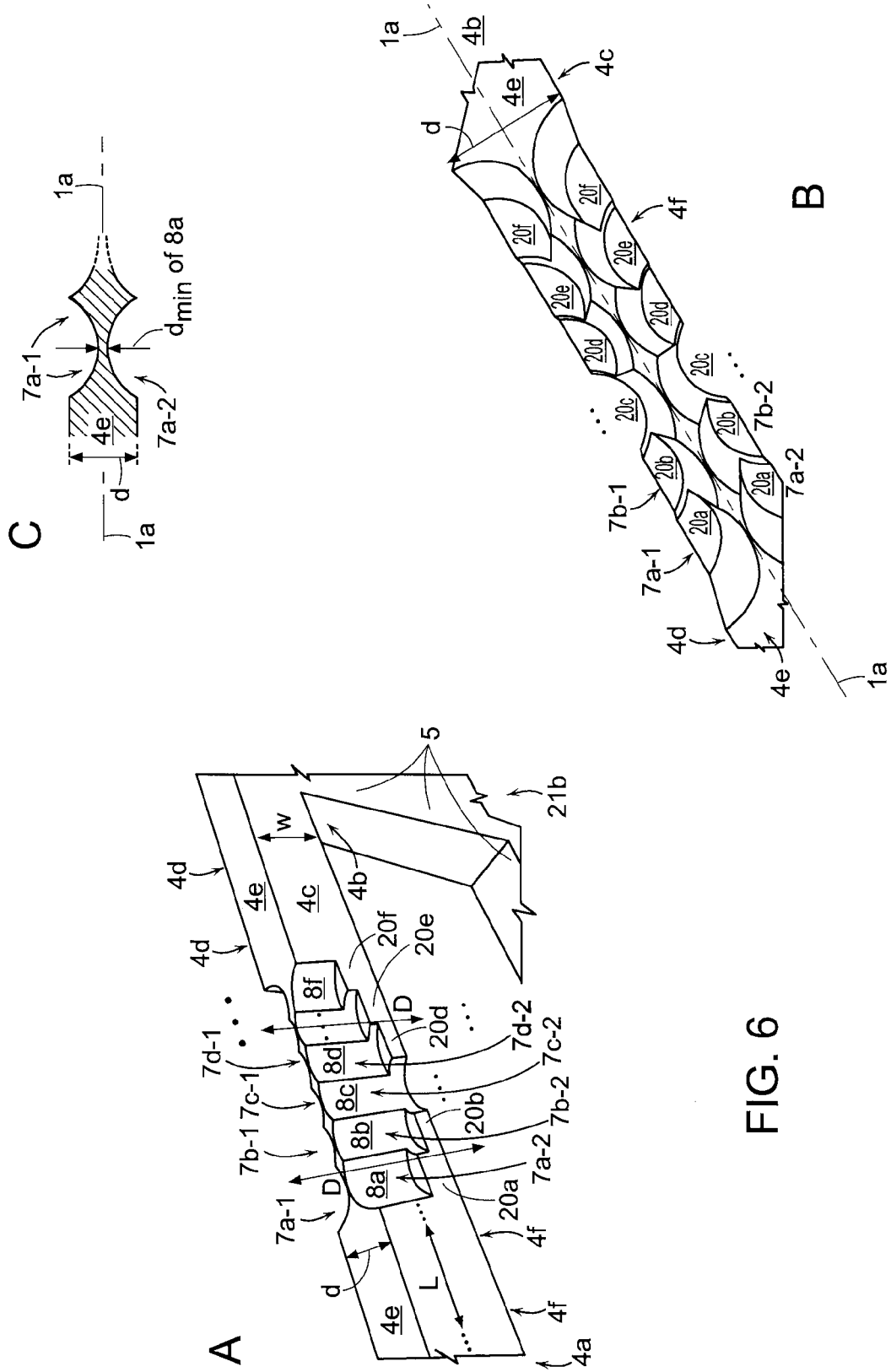

FIG. 6: A cantilever beam after the detachment and after the laser-based thinning FIG. 7: An exemplary arrangement according to the invention.

FIG. 8: Another exemplary arrangement according to the invention.

In the figures, identical reference signs correspond to identical features.

FIG. 1 shows a flat substrate 1 with a thickness of d=150 micrometer made from silicon. Deflected by a galvanometer scanner 10 (not shown, compare FIG. 7), a laser beam 2 of a 532 nm YVO$_4$ laser 11 (not shown, compare FIG. 7) is directed towards the substrate 1 with a fluence of 0.8 J/cm$^2$. By deflecting the laser beam 2 in the plane of the substrate with the galvanometer scanner 10, the contour of the basic structure 3 (compare FIG. 2) to be detached from the substrate 1 is defined. FIG. 1 shows examples for parts of such basic structures to be detached from the substrate; some of them are denoted with "1", "2" and "3", the latter numbers concurrently denoting labels which can be introduced into the supporting structure 5 (FIG. 2) of a basic structure 3 for allowing a better differentiation between different basic structures 3.

As can be seen in FIG. 1, the energy, wavelength, repetition rate, and scan speed of the laser beam 2 is selected in such a manner that the laser beam 2 cuts through the whole thickness d of the substrate 1. Typical values for advantageous repetition rates and scan speed are 30 kHz and 100 mm/min, respectively.

FIG. 2 (dark parts, the light parts show a background on which the basic structure is put) is an example for a finished basic structure 3, i.e. a basic structure 3 completely detached from the substrate 1. The basic structure 3 comprises a supporting structure 5 of an essentially half ring shape, in which (at the outer circumference of the arcuate part) two notches 21a, 21b have been introduced at essentially opposing sides during the detaching step. These two notches 21a, 21b are intended to simplify the clamping of the supporting structure 5 of the basic structure 3 by the mount 6 (FIG. 3). The notches 21a, 21b can be introduced (when machining different basic structures 3) in such a manner that the upper edge (or the front face 4e, respectively, compare FIG. 3) of each basic structure 3 protrudes (with respect to the surface of the mount 6, compare FIG. 3) by the same absolute value. This simplifies the processing because it allows to focus the laser beam at the same position for each different basic structure 3 to be processed.

At the side opposing the two notches 21a, 21b, i.e. along the diameter of the half ring of the supporting structure 5, the basic structure 3 comprises a cantilever beam 4 with an essentially rectangular cross-section (seen perpendicular to the shown plane, i.e. perpendicular to the substrate's plane 1a of the cantilever beam 4—compare FIG. 6—, and perpendicular to the longitudinal extension L of the cantilever beam 4). Thus, the basic structure 3 is manufactured in form of one single piece comprising the elements 4 and 5, wherein the cantilever beam 4 is connected, at its two opposing ends 4a and 4b, with the inner circumference of the essentially ring-shaped supporting structure 5.

The upturned face of the cantilever beam 4 visible in FIG. 2 is one of the two opposing lateral faces to be further thinned in the laser-based thinning step (denoted with the reference sign 4c). The two front faces of the cantilever beam 4 which are aligned perpendicular to the lateral faces 4c and 4d (compare FIG. 6) are denoted with the reference signs 4e and 4f.

As the cantilever beam 4 (in a further thinned form) finally results in the desired sample for microstructural materials diagnostics, also the reference sign P is provided in FIG. 2.

The sketch of FIG. 2a shows a state of the basic structure of FIG. 2 before it has been completely detached (as shown in FIG. 2) from the substrate 1. As can be seen in FIG. 2a, the basic structure 3 is still and exclusively connected with a holding frame 1F via two holding bases 51a and 51b adjacent to both opposing ends 4a and 4b of the beam 4 (see FIG. 2). Here, the holding frame 1F is a rectangular part of the substrate 1 encompassing the basic structure 3, where the holding frame 1F has already been detached from the substrate 1 based on a laser machining process. However, also the entire substrate 1 can be used as the or can be identical to the holding frame 1F. The holding bases 51a, 51b connect the holding frame 1F with the basic structure 3 at the side of the supported structure 4 and adjacent to the supported structure 4. The two holding bases 51a and 51b constitute part of the supporting structure 5 still connecting the basic structure 3 with the holding frame 1F.

In a first period of the detaching step, the basic structure 3 is detached on all sides from the holding frame 1F except for the two holding bases 51a, 51b by using the laser 11 (compare FIGS. 7 and 8) with full power, for example with 3 W or 10 W and a beam diameter of 20 µm. This full power machining has the advantage that most of the contour of the basic structure 3 can be detached from the substrate 1 and the holding frame 1F, resp., in a very fast and efficient manner. During this first period of the detaching step, the holding frame and the to-be-detached basic structure 3 are exposed to a jet of compressed air, $N_2$ or rare gas in order to avoid debris deposition, i.e. to avoid that debris generated when cutting-out the contour of the basic structure 3 reverts back to the basic structure leading to an undesired interaction with the cutting laser beam (especially during the second period of the detaching step). In this first period of the detaching step, the two holding bases 51a, 51b confer the necessary stability to the basic structure 3 during the exposure to the gas jet (thus especially preventing the basic structure from flying away and being destroyed due to the gas jet).

In a second period of the detaching step, the power of the laser 11 is reduced (for example to some 10 to 50 percent of the laser power used in the first period described above). Afterwards, the comparatively coarse cutting edges of the two front faces 4e, 4f generated during the first period of the detaching step are reworked with this laser power in order to smooth them. Alternatively, in the first period of the detaching step with high laser power, the generation of the two front faces 4e, 4f can be omitted so that these faces 4e, 4f are generated with the reduced power. In the second period of the detaching step the reduced power is used in order to attain a cutting with optimized edge-accuracy.

Alternatively, other laser parameters and/or process parameters, including but not limited to pulse repetition rate, scanning speed, pulse length, beam dimensions are varied between the two periods so as to achieve a quick, but coarse cutting of the basic structure without the two front faces 4e, 4f and a smoother, more accurate but slower cutting of the front faces 4e, 4f. Optionally, the holding frame and the to-be-detached basic structure 3 are exposed to a jet of compressed air, N2 or noble gas during this second period of the detaching step and/or during the subsequent thinning step to avoid debris deposition.

Finally, in a third period of the detaching step, the basic structure 3 is fully detached on all sides from the holding frame 1F by destroying the two holding bases 51a, 51b between the supporting structure 5 and the frame 1F either with the laser 11 or by quarrying the basic structure 3 out.

If Si is used as the material for the substrate 1, a width of the two holding bases (seen parallel to the faces 4e, 4f) of 25 µm (or more) is sufficient to provide sufficient resistance to the blowing.

FIG. 3 shows an exemplary mount 6 which is configured to clamp the supporting structure 5 of the basic structure 3 in-between its two clamping jaws 6a and 6b in order to guarantee a fixing of the basic structure 3 relative to the mount 6. As can be seen in FIG. 3a, one of the clamping jaws, the jaw 6a, is configured with two engagement sections 22a and 22b, which engagement sections correspond to the notches 21a, 21b and are therefore formed so as to be vertically engaged with these notches. The other one of the clamping jaws, the jaw 6b, is provided with two protrusions 23a and 23b which are opposing the engagement sections 22a and 22b and which are configured so as to (horizontally) engage in the engagement sections 22a and 22b when the two jaws 6a, 6b are closing. In the closed state (FIG. 3b) of the two jaws 6a, 6b, the supporting structure 5 of the basic structure 3, which has been moved into the engagement sections 22a and 22b from above, is clamped in-between wall parts of the engagement sections 22a, 22b on the one hand, and the protrusions 23a, 23b on the other hand, so as to be fixed (relative to the mount 6) in a predefined position.

As FIG. 3a shows, several pairs of engagement sections 22 and corresponding pairs of opposing protrusions 23 can be provided in order to fix several basic structures 3 relative to the mount 6 at the same time.

FIG. 3b shows the closed state of the mount 6, wherein three different basic structures 3a to 3c are fixed relative to the mount 6. As can be seen (the corresponding bearings are not shown) the (closed) mount 6 can be tilted at least partly (for example by ±10°) around the horizontal tilt axis R and can also be tilted (for example also by ±7°) around another horizontal axis T being arranged perpendicular to the tilt axis T. This allows a nearly free positioning of the basic structures 3a to 3c in the world coordinate system and relative to the irradiating laser beam 2, respectively, in a nearly arbitrary pose. Especially, the cantilever beam 4 can be positioned in such a manner that perpendicular flanks (compare FIG. 5) can be cut also with a galvanometer scanner (compare FIGS. 7 and 8). A tilting back and forth around the axis T and/or the axis R also allows the prevention of undesired curtaining effects.

The thickness d of the basic structure of for example 100 to 150 micrometer guarantees that the clamping of the basic structure 3 between the clamping jaws 6a, 6b of the mount 6 does not damage the basic structure. The notches 21, on the one hand, and the engagement sections 22 and the protrusions 23, on the other hand, allow a clamping of the basic structure for the sample P in such a manner that the radius of the supporting structure corresponds to the radius in the engagement sections 22 of the clamping jaw 6a so that an exact positioning and fixing of the supporting structure between the two clamping jaws 6a, 6b is possible and that an undesired rotation of the basic structure relative to the mount 6 can be avoided. The pose of the clamped basic structure 3 then defines the incident angle of the thinning laser beam 2 (and also of the further thinning ion beam for the post-processing, if necessary). Lateral spare areas in the jaws 6a, 6b besides and below the area in which the supporting structure is clamped prevent a re-deposition of a plated material and the damaging of the mount 6, respectively.

For a post-thinning with an ion beam, the already laser-thinned basic structure (compare FIG. 6) can also be held by a different mount which is provided by a specific ion beam etching system, for example a precision ion polishing system as is known from the prior art. However, the mount 6 of FIG. 3 can be used during the laser-based thinning step as well as during a subsequent, additional thinning-post-processing to further thin the already laser-thinned sections with help of an ion beam.

FIG. 5 shows how to realize perpendicular flanks and sidewalls, respectively, for channel structures to be introduced into the lateral faces of the cantilever beam (i.e. flanks of the introduced structures which are parallel to the substrate's plane 1a of the cantilever beam 4, compare FIG. 6). In other words, FIG. 5 shows how a grazing incidence of the laser beam with respect to the lateral faces of the cantilever beam can be realized, in which the boundary area 2b of the incident laser beam 2 grazes the surface of the cantilever beam 4 which is to be processed in a parallel manner and in a predefined depth. In FIG. 5, the substrate's plane 1a of the supported structure (compare FIG. 6) is visible (in a sectional view) as a line.

FIG. 5a shows the situation when the laser beam 2 impinges vertically and close to an edge onto a surface of the cantilever beam 4 (here: the front face 4e, compare FIG. 6) which is arranged perpendicular to the desired flank to be introduced into the lateral face 4c of the cantilever beam 4. The angle between the central beam axis and main beam axis, respectively, 2a of the laser beam 2 on the one hand, and the front face 4e irradiated by the laser beam 2 on the other hand, therefore equals 90°. When the laser beam 2 is focussed in the manner shown in FIG. 5a onto the surface 4e (compare focusing optics 9 in FIG. 7), due to the coupling of the laser beam 2 into an establishing flank, a beam broadening angle of $2\alpha$ results. Consequently, if the main beam axis 2a is perpendicular to the surface 4e, i.e. parallel to the substrate's plane 1a of the cantilever beam 4, that is when there is no tilt angle between the axis 2a and the plane 1a ($\alpha=0°$, compare FIG. 5a), the groove which is introduced by material removal into the surface 4e of the cantilever beam essentially has a V-shape (compare FIG. 4) with a flank angle between the irradiated surface 4e on the one hand and the flank introduced into the material of the cantilever beam 4 on the other hand of 90°+(half of the beam broadening angle $2\alpha$)=100° in the shown case with a broadening angle $2\alpha=20°$.

In order to realize flanks of the introduced channel structures 7 (compare FIG. 6) which are aligned perpendicular to the front faces 4e, 4f, i.e. parallel to the lateral faces 4c, 4d to be cut with the laser beam in a parallel manner, the main beam axis 2a of the beam 2 has to be tilted, relative to the substrate's plane 1a of the cantilever beam 4, by a tilting angle $\alpha$ which equals half of the beam-broadening angle $2\alpha$ of the beam 2 impinging on the surface 4e. As FIG. 5b shows, then a flank can be introduced with a flank angle of 90° into the lateral face 4c. In order to introduce perpendicular flanks for example in the form of several channel structures 7 (FIG. 6) on both opposing lateral faces 4c and 4d, before grazing also the opposing lateral face 4d with the laser beam 2 (having already introduced perpendicular flanks in the lateral face 4c with help of the boundary area 2b of the beam 2), the basic structure 3 with its cantilever beam 4 has to be tilted (with the mount 6) relative to the main beam axis 2a in the opposite direction of the tilt status shown in FIG. 5b by an angle of $2\alpha$ (seen relative to the cantilever beam 4 in a state already tilted by the angle of a). After that (and after an adequate translation of the basic structure 3 with the mount 6), the boundary area 2b of the incident laser beam 2 can be used again to cut also a perpendicular flank into the lateral face 4d of the cantilever beam 4. Tilting the cantilever beam 4 by $\pm\alpha$ in two opposite directions therefore allows the introduction of perpendicular flanks on both opposing lateral faces 4c, 4d.

Therefore, the laser-based thinning step can be performed on both lateral faces of the cantilever beam 4 in order to further (in a plane-parallel manner) reduce the thickness of the sample P (i.e. to reduce the thickness of the area of the cantilever beam 4 which will constitute the sample essentially below the thickness d of the substrate 1). For example, with a substrate thickness d=150 micrometers, introducing thin channel structures from both sides (FIG. 6) can reduce the sample thickness in the remaining sections 8 to a value $d_{min}<20$ micrometer. Deflected by a galvanometer scanner 10 (FIG. 7), the laser beam can be directed onto a front face of the cantilever beam twice with identical tilt angles $\alpha$ of for example 10°, but by tilting the cantilever beam 4 and its plane 1a (relative to the main beam axis 2a) in two opposite directions as shown in FIG. 5b. A complicated generation of a parallel cutting gap utilizing a dedicated optics using a tiltable and rotatable drilling head so that the impinging beam 2 is concurrently tilted and rotated in adequate positions 2-1 and 2-2 (see FIG. 5c) can therefore be avoided. As shown in FIG. 5b, according to the invention, a simple thinning to realize remaining sections 8 aligned parallel to the former lateral faces 4c and 4d (compare FIG. 6) is possible when using the two step approach with a tilting of the cantilever beam twice, i.e. in opposite directions.

It is therefore technically only necessary to incline the basic structure by a defined angle $\alpha$ between its plane 1a and the main beam axis 2a. To determine the necessary tilt angle $\alpha$ (which depends upon the geometrical parameters of the impinging laser beam 2) the following procedure is possible: Before or after the detaching of the basic structure from the substrate 1, several holes are drilled, with the laser beam 2, into the substrate 1. These holes can then be optically surveyed (with help of a camera based surveying system) with respect to the hole diameter on the surface of the substrate 1 on which the laser beam 2 impinges on the one hand, and the hole diameter on the opposing surface of the substrate 1 (output side), on the other hand. The necessary tilt angle α can then be calculated from these different hole diameters.

FIG. 6a shows a lateral view and FIGS. 6b and 6c show a bird's eye view of a cantilever beam 4 after the detaching step and the laser-based thinning step of the present invention (and before a possible additional post-processing thinning with an ion beam). Several parallel channel structures with channel end supports 20 of different extensions, i.e. of different channel depths in the material of the cantilever beam 4 are shown. The different channel depth improves the stability of the shown thinned cantilever beam structure. Whereas, in FIG. 6, the several channel structures 7 are introduced exactly parallel to the central plane 1a of the cantilever beam 4, slightly wedge-shaped flanks (i.e. introducing the walls of the channel structures 7 not exactly parallel to the plane 1a, but slightly tilted) may additionally improve the stability of the shown cantilever beam.

FIG. 6 shows the laser-based thinning of a cantilever beam 4 with a rectangular cross-section (seen perpendicular to the longitudinal extension L of the beam 4). The thickness d of the beam 4 perpendicular to the central plane (substrate's plane 1a) of the beam 4 is d=150 micrometers (distance between the two opposing lateral faces 4c and 4d). The width w of the cantilever beam (distance between the two front faces 4e and 4f, i.e. extension of the cantilever beam 4 in the plane 1a and perpendicular to the longitudinal extension L) equals w=200 micrometers in the shown structure. The two ends 4a and 4b of the beam 4, i.e. the connecting sections with the supporting structure 5 (as well as the latter) are only shown in parts.

Along the longitudinal extension L, parallel to the plane 1a and on both opposing lateral faces 4c and 4d, several channel structures 7a to 7f have been cut into the surfaces 4c and 4d of the beam 4 by grazing incidence of the beam 2 on the two opposing faces 4c and 4d. The impinging laser beam has been positioned, in order to introduce the channel structures 7, in such a manner that remaining sections 8, remaining after the laser-based thinning in the centre of the material of the beam 4 (seen in the thickness direction d of the beam 4), remain in a symmetrical manner with respect to the central plane 1a (compare especially FIGS. 6b and 6c). The two series 7x-1, 7x-2 of channel structures which have been introduced on both sides of the beam 4 are arranged (seen in L direction) in a symmetrical manner with respect to the two opposing ends 4a and 4b of the beam 4. Seen along the L direction, on each of the faces 4c and 4d, the channel structures 7 have been introduced in such a way that their longitudinal direction D is aligned perpendicular to the longitudinal extension L and parallel to the plane 1a. The channel structures introduced into the face 4c are denoted by 7a-2, 7b-2, . . . and the channel structures of the opposite side in the face 4d are denoted by 7a-1, 7b-1, . . . Directly adjacent channel structures of one and the same lateral face (for example the structures 7a-1 and 7b-1) have been introduced in an overlapping manner: The diameter of a channel structure (cross-sectional extension perpendicular to the longitudinal direction D) is 10 to 20 micrometers in the present case. The centres of two directly adjacent channel structures seen along the direction L have a distance of 20 to 50 micrometers, or less, or more.

This introduction of the channel structures 7 leads to remaining wall sections 8a, 8b, . . . between each pair of opposing channel structures of the two opposing faces (for example the wall section 8a between the channel structure 7a-1 of face 4d on the one hand, and channel structure 7a-2 of face 4c on the other hand) which have a minimum thickness of $d_{min}$=0.5 to 10 micrometers (compare FIG. 6c) in the present case.

Seen along the width direction w of the cantilever beam 4 (i.e. along the longitudinal direction D of the channel structures 7), the channel structures 7 are introduced, into the material of the beam 4, with a different depth: Only the (approximately) central channel structures 7c-1 and 7c-2 have been introduced over the whole width w of the cantilever beam 4. On the lower side (i.e. the lower front face 4f) of the channel structures 7a, 7b, 7d, 7e and 7f of both faces 4c, 4d, channel end supports 20a, 20b, . . . have been left after the laser-based thinning by not removing cantilever beam material in order to further stabilize the shown laser-thinned structure. From the centre to the two outer sides (seen along direction L) the height of the channel end supports 20 of the channel structures 7 increases approximately linearly.

During the thinning-postprocessing with an ion-beam, the ion beam can be irradiated essentially parallel (except for the tilt angle β) along the longitudinal direction of a/the channel structure(s) 7 introduced into the lateral faces 4c, 4d of the cantilever beam 4 such that the direction of incidence of the ion-beam points from the lower side (face 4f) to the upper side (face 4e) of the cantilever beam (i.e. the bar) 4, i.e. faces from a side 4f of the cantilever beam 4 on which the cantilever beam 4 is not tapered to a side 4e of the cantilever beam 4 on which the cantilever beam is tapered 20a, 20b, . . .

However, when detaching the supported structure 4 or the cantilever beam, respectively, with an arcuate shape (seen along L) and with thickenings at both ends 4a, 4b, the channel structures 7 can also be introduced, into the material of the beam 4, with the same depths without deteriorating the stability of the thinned structure.

For the further thinning of the already thinned remaining sections 8, as already described, for example an ion beam irradiated onto the remaining sections 8 with an acute angle can be used.

FIG. 6 shows that the thinned, remaining sections 8 can be stabilized if parallel channels 7 with different depths are introduced into the material of the beam 4. The shown structure is compatible with a post-thinning based on an ion beam which is irradiated essentially along the direction D, but with a slight tilt angle with respect to the plane 1a. Therefore, the shown structure can be used for a further thinning in a focussed ion beam thinning system. As several thinned sections 8 are provided, several electron beam transparent (further thinned) sections can be generated in the focussed ion beam system practically at the same time. With the further ion beam based thinning, the laser-thinned sections 8 can be further thinned down to a thickness d of approximately 10 to 100 nm.

It is also possible to realize parallel channels 7 with wedge-shaped flanks along the direction D or frustum-shaped channels for further stabilizing the shown structure. It is possible to introduce channel structures 7 alternately from the upper side (face 4e) and from the lower side (face 4f), i.e. to provide (seen in direction D) the channel end supports 20 alternately on opposing ends. The post-thinning based on an ion beam can be performed with arbitrary ion beam systems, especially based on broad or focussed ion beams.

With the aforementioned laser processing, thicknesses $d_{min}$ of the remaining sections 8 between 5 to 15 micrometers can be realized (whereas in the prior art, only structures with a minimum thickness $d_{min}$ which is approximately two to four times higher can be realized). Consequently, with the present invention, the post-thinning of the remaining sections 8 with an ion beam can be performed much faster.

FIG. 7 shows the structure of one possible arrangement for manufacturing a sample P, i.e. for laser-processing the substrate 1 and for laser-thinning the cantilever beam 4 (the subsequent post-thinning with an ion beam is not shown).

The beam 2 of the laser 11 is irradiated onto a focusing optics 9 (preferably comprising a Varioscan focusing lens) and, on the beam output side of the focusing optics 9, in a beam deflector 10 (here: a galvanometer scanner 10). The focusing optics 9 and the scanner 10 (together with the beam shaping element 31, see below) constitute beam-forming device (here: an optical device) 12 positioned in the optical path of the laser 11 which is adapted to irradiate the substrate 1 and the cantilever beam 4 in order to process these elements 1, 4. The construction of a galvanometer scanner 10 with two rotatable deflection mirrors 10a and 10b is well-known for the skilled person. Instead of using a galvanometer scanner 10 to deflect the beam 2 relative to substrate 1 and cantilever beam 4, respectively, also an x-y-z table (not shown) translating the substrate 1 and the cantilever beam 4, respectively, relative to the momentary position and orientation of the beam 2 can be used.

Between the laser 11 and the focusing optics 9, a beam expander 30 (for example: telescope) is introduced in the path of the beam 2 in order to define the spot diameter of the beam 2 in a desired manner. Between the focusing optics 9 and the galvanometer scanner 10, a beam shaping element 31 (here: a cylindrical lens) is introduced in the course of the beam 2 in order to define the cross sectional shape of the beam 2 (and therefore of the channel structures 7 to be introduced into the cantilever beam 4) in a desired manner (here: elliptical).

During the detaching step, the laser beam 2 is deflected 2' (with scanner 10) onto the surface of the substrate 1 and moved across this surface along the contour of the basic structure 3 to be detached (the contour of the supporting structure to be detached from the substrate 1 is denoted with 5' and the contour of the cantilever beam to be detached from the substrate 1 is denoted with 4'). In order to avoid an undesired movement of the substrate 1 relative to the housing of the galvanometer scanner 10, a second mount 13 is provided which uses braces 13a and 13b to fix the substrate 1 on its surface (such mounts 13 are well-known to the skilled person).

Having finished the detaching step, i.e. having (manually by an operator or also automatically with an adequate positioning system) clamped the finished basic structure 3 into the two clamping jaws 6a and 6b of the mount 6 (FIG. 3), the supporting structure 5 (and therefore also the cantilever bar 4) is fixed by the mount 6. Due to the notches 21a, 21b, the upper edge of the cantilever beam 4 is positioned, above the upper surface of the mount 6, in a predefined distance. Then, during the laser-thinning step, the laser beam 2 can be deflected 2" over the surfaces of the cantilever 4 as desired in order to generate the structures shown in FIG. 6. The relative movement between the cantilever beam 4, on the one hand, and the laser beam 2, 2" impinging on it on the other hand, is defined in the desired manner based on the deflection of the rotatable mirrors 10a and 10b of the scanner 10, on the one hand, and by tilting and/or rotating the basic structure 3 with the mount 6 (compare the axes T and R thereof in FIG. 3) on the other hand.

Not shown in the arrangement of FIG. 7 is a compressed air irrigation and/or suction system, an observation system (vision system comprising a digital camera for visual inspection, compare FIG. 8) and a controlling system (personal computer or the like) to control all system components and to control the processing during the steps of the method according to the invention. Only the manual interaction of conveying the finished basic structure 3 from the second mount 13 to the mount 6 is necessary (if no automatic transfer is possible). Supported by Finite Element Modelling (FEM), the stability of the sample can be estimated in order to optimize the sample geometry generated during the laser-based thinning process (and the post-thinning with the ion beam).

The shown arrangement can be inherently realized directly in an existing ion beam etching system, for example in a precision ion polishing system which is known from the prior art (the laser beam 2 is then coupled in an adequate way into this system). Laser machining under vacuum should be beneficial while implementation into a vacuum system is more costly.

The arrangement and the process according to the invention can also be introduced into a system for processing a substrate with a focused ion beam (Ga-ion source or high-rate noble gas ion source).

The present invention is applicable in a universal manner in the area of processing planar substrates. Stable samples which can easily be handled can be generated. The samples can also be labelled based on the present invention with the laser beam in order to avoid a confusion of samples. The arrangement can be realized at limited costs. Processes which have to be performed before a post-thinning with an ion beam can be replaced by the present invention, wherein the steps of the present invention can be performed much faster (some minutes instead of 4 to 8 hours) compared to the replaced processes.

FIG. 8 shows the structure of another possible arrangement for manufacturing a sample P, i.e. for laser-processing the substrate 1 and for laser-thinning the cantilever beam 4 (the subsequent post-thinning with an ion beam is not shown). Basically, the arrangement is the same as the one shown in FIG. 7 so that only the differences are described (therefore, also the beam output side of the galvanometer scanner 10 is shown).

According to FIG. 8a, during the detaching step, the second mount 13 is positioned underneath scanner 10. Having finished the detaching step, the second mount 13 is removed (with the rest of the substrate 1), mount 6 is introduced, the basic structure 3 is clamped within the latter and the laser-processing of the thinning step is performed (FIG. 8b). 32 denotes an observation system (vision system comprising a digital camera). System 32 can be used for visual inspection of the substrate 1 during the detaching step and of the cantilever beam 4 during the laser-thinning step. Especially, the positioning of the cantilever beam 4 can be controlled with this system during, before, and after the laser-thinning step. During the laser-thinning, tilting the clamped basic structure 3 with its cantilever beam 4 back and forth around the axis T avoids undesired curtaining effects. The controlling of the steepness of the lateral faces 4c, 4d relative to the impinging beam 2, 2" is performed by (slightly) tilting the cantilever beam 4 around the R axis.

The present invention can be also used to process substrates 1 in form of cross sectional samples or gradient materials. Especially, also the homogeneity of a sample can be controlled at different positions. The channel structures 7 can be introduced perpendicularly as well as diagonally, i.e. in a crossing manner. Additionally (not shown in the Figures), a beam splitter can be used in order to simultaneously direct two (partial) beams onto two opposing lateral faces 4c, 4d of the cantilever beam 4 in a grazing manner. This avoids the necessity to tilt the cantilever beam 4 twice in opposite directions by angles ±α in order to process both of the opposing lateral faces. The described laser-processing can also easily be used to label the basic structure (for example in a manner described in U.S. Pat. No. 7,095,024 B2).

What is claimed is:

1. A method for manufacturing a sample for microstructural materials diagnostics comprising:
   detaching a basic structure from a substrate by irradiating the substrate with a laser beam as an high-energy beam so that the detached basic structure comprises a supported structure and a supporting structure, wherein the supported structure is supported by the supporting structure and wherein the supporting structure is configured to be held by a jig, and
   thinning the supported structure at least in sections by cutting its surface with the laser beam, wherein
   the thinning of the supported structure is carried out by irradiating the laser beam onto the supported structure in such a way that a boundary area of the incident laser beam grazes the supported structure in a direction parallel to the substrate's plane of the supported structure, wherein the main beam axis of the laser beam is tilted, relative to the substrate's plane of the supported structure, by an angle α≥5° and α≤20°, wherein the thinning of the supported structure is carried out by introducing, due to laser-beam-induced material removal, at least one channel structure(s) into the surface of the supported structure, into at least one of lateral faces and/or of front faces of the supported structure, or into two opposing lateral faces of the supported structure, wherein the longitudinal direction of the channel structure(s) is/are aligned perpendicular to the longitudinal extension of the supported structure, wherein said at least one channel structure(s) has a diameter of 10-20 micrometers, and a centre distance to an adjacent channel structure(s) of 20-50 micrometers.

2. The method according to claim 1, wherein after the thinning of the supported structure, a thinning postprocessing is performed in order to further thin a section or sections of the supported structure which has/have already been thinned by the cutting incidence of the laser beam in said laser beam based thinning, wherein the thinning postprocessing is performed by ion beam etching and/or by irradiating the section of the supported structure which has/have already been thinned by the cutting incidence of the laser beam with an ion beam.

3. The method according to claim 2, wherein after the thinning of the supported structure, the thinning postprocessing is performed in order to further thin a remaining section or remaining sections which remain(s), after the laser-beam-based thinning, between two channel structures introduced into two opposing lateral faces of the supported structure and opposing each other and/or in that the ion beam is irradiated onto and/or into the section(s) of the supported structure which has/have already been thinned by the cutting in at least one of the following manners:
   as a focused or broad ion beam, with a grazing incidence, and/or with a glancing angle β>0°, between the substrate's plane of the supported structure and the main beam axis of the ion beam.

4. The method according to claim 3, wherein said glancing angel β≥2° and ≤15°.

5. The method according to claim 3, wherein said glancing angle β=4°.

6. The method according to claim 1, wherein the thinning of the supported structure is carried out by irradiating the laser beam onto the supported structure in such a way that a boundary area of the incident laser beam grazes, the supported structure in a direction parallel to the substrate's plane of the supported structure, wherein a main beam axis of the laser beam is tilted, relative to the substrate's plane of the supported structure, by half of the broadening angle 2α of the laser beam and/or by an angle α≥5° and α≤20°.

7. The method according to claim 6, wherein the angle α≥5° and α≤20°.

8. The method according to claim 6, wherein the angle α≥8° and α≤12°.

9. The method according to claim 6, wherein the angle α=10°.

10. The method according to claim 1, wherein seen along the longitudinal extension of the supported structure, several channel structures are introduced parallel to each other and in a spaced relationship to each other into the surface of the supported structure, into at least one of the lateral faces of the supported structure, or into both of the two opposing lateral faces of the supported structure, wherein when introducing several channel structures in this manner into both of the two opposing lateral faces of the supported structure, for each channel structure introduced into one of the two opposing lateral faces, another channel structure is introduced into the other of the two opposing lateral faces in a symmetrical manner with respect to the substrate's plane of the supported structure.

11. The method according to claim 10, wherein the several channel structures are introduced into the lateral face(s) of the supported structure in such a manner that at least one of the channel structures is not introduced, seen in the longitudinal direction of the respective channel structure, along width of the supported structure, wherein those channel structures of both of the two opposing lateral faces which are introduced adjacent to the ends of the supported structure are not introduced along the whole extension of the supported structure, and/or in that the several channel structures are introduced into the lateral face(s) of the supported structure in such a manner that channel structures are, seen in the longitudinal direction of the respective channel structure, emanating from both front faces of the supported structure, or emanating alternately from one front face and from another front face of the supported structure.

12. The method according to claim 1, wherein thickness of the substrate perpendicular to the substrate's plane and/or thickness of the supported structure perpendicular to the substrate's plane of the supported structure is, including the limits, between 50 μm and 500 μm, and/or in that the substrate is a ground plate, and/or in that the width of the supported structure, that is the dimension of the supported structure perpendicular to its longitudinal extension and perpendicular to its thickness, is, including the limits, between 100 μm and 2500 μm.

13. The method according to claim 1, wherein section(s) of the supported structure which are thinned by the cutting incidence of the laser beam in the thinning, a remaining section or remaining sections which remain(s), after the laser-beam-based thinning, between two channel structures introduced into two opposing lateral faces of the supported structure and opposing each other, has/have a minimum thickness perpendicular to the substrate's plane of the supported structure which is, including the limits, between 0.5 μm and 50 μm.

14. The method according to claim 1, wherein after the detaching of the basic structure from the substrate, the laser beam is focused by a focusing optics and/or is deflected by a galvanometer scanner before it is irradiated onto the supported structure and/or the supported structure is moved, relative to the impinging laser beam, with an x-y-z table or a scanning stage in order to realize the cutting incidence of the laser beam onto the supported structure during said thinning and/or in that after the detaching of the basic structure from the substrate, the supporting structure of the basic structure is held by the jig, the latter being tiltable around a first axis and/or tiltable around a second axis, and is positioned, with the jig, relative to the laser beam in order to realize the cutting incidence of the laser beam onto the supported structure in said thinning.

15. The method according to claim 1, wherein the detaching of the basic structure is performed as follows: the basic structure is at first detached on all sides from a holding frame except for at least one holding base(s) still connecting the basic structure with the holding frame, before the holding base(s) is/are destroyed in order to completely detach the basic structure from the holding frame, wherein the holding frame is the substrate or is a part of the substrate, a part of the substrate which has already been detached from the substrate.

16. The method according to claim 1, wherein said angle $\alpha \geq 8°$ and $\alpha \leq 12°$.

17. The method according to claim 1, wherein said angle $\alpha = 10°$.

18. A method for manufacturing a sample for microstructural materials diagnostics comprising:
 detaching a basic structure from a substrate by irradiating the substrate with a laser beam as an high-energy beam so that the detached basic structure comprises a supported structure and a supporting structure, wherein the supported structure is supported by the supporting structure and wherein the supporting structure is configured to be held by a jig, and
 thinning the supported structure at least in sections by cutting its surface with the laser beam, wherein
  the thinning of the supported structure is carried out by irradiating the laser beam onto the supported structure in such a way that a boundary area of the incident laser beam grazes the supported structure in a direction parallel to the substrate's plane of the supported structure, wherein the main beam axis of the laser beam is tilted, relative to the substrate's plane of the supported structure, by an angle $\alpha \geq 5°$ and $\alpha \leq 20°$,
 wherein the thinning of the supported structure is carried out by introducing, due to laser-beam-induced material removal, two channel structures into the surface of the supported structure,
 wherein section(s) of the supported structure which are thinned by the cutting incidence of the laser beam in the thinning, a remaining section or remaining sections which remain(s), after the laser-beam-based thinning, between the two channel structures introduced into two opposing lateral faces of the supported structure and opposing each other, has/have a minimum thickness perpendicular to the substrate's plane of the supported structure which is, including the limits, between 0.5 μm and 50 μm, wherein said two channel structures have a diameter of 10-20 micrometers, and a centre distance between said two channel structures of 20-50 micrometers.

* * * * *